(12) United States Patent
Högnelid et al.

(10) Patent No.: US 6,253,765 B1
(45) Date of Patent: Jul. 3, 2001

(54) METHOD FOR DETERMINING THE VOLUME OF A TUBING SYSTEM AND A BREATHING APPARATUS SYSTEM

(75) Inventors: Kurt Högnelid; Göran Skog, both of Bromma (SE)

(73) Assignee: Siemens Elema AB, Solna (SE)

( * ) Notice: Subject to any disclaimer, the term of this patent is extended or adjusted under 35 U.S.C. 154(b) by 0 days.

(21) Appl. No.: 09/333,619

(22) Filed: Jun. 15, 1999

(30) Foreign Application Priority Data

Jun. 15, 1998 (SE) .................................................. 9802122

(51) Int. Cl.$^7$ .................................................. A61M 16/00
(52) U.S. Cl. .............................. 128/204.18; 128/204.21; 128/204.22
(58) Field of Search ................... 128/204.18, 204.21, 128/204.22

(56) References Cited

U.S. PATENT DOCUMENTS

| 3,729,000 | 4/1973 | Bell . |
| 3,923,056 | 12/1975 | Bingmann et al. . |
| 4,819,629 | * 4/1989 | Jonson ............................ 128/203.22 |
| 5,738,090 | * 4/1998 | Lachmann et al. ............. 128/204.23 |

* cited by examiner

Primary Examiner—Glenn K. Dawson
Assistant Examiner—Mital Patel
(74) Attorney, Agent, or Firm—Schiff Hardin & Waite

(57) ABSTRACT

In a method for determining the elastic volume (representing the gas which must be added to compensate for the compression of gas occurring in the tubing system) of a tubing system connected to a patient without the patient's lungs and airways entering into the determination, a determination of the volume of the tubing system is made at two different pressures during one breathing cycle and the elastic volume is calculated from the volumes thus determined. The volume of the tubing system can be established by adding a predetermined flow of a first gas to the tubing system, while constant pressure is maintained in the tubing system, when the flow of breathing gas to/from the patient is virtually zero, determining when the first gas starts flowing out of the tubing system and determining the volume of the added first gas, this volume constituting the volume of the tubing system.

29 Claims, 2 Drawing Sheets

METHOD FOR DETERMINING THE VOLUME OF A TUBING SYSTEM AND A BREATHING APPARATUS SYSTEM

BACKGROUND OF THE INVENTION

1. Field of the Invention

The present invention relates to a method for determining the volume of a tubing system connected to a ventilator and to a patient. The present invention also relates to a method for determining an elastic volume of a tubing system connected to a ventilator and to a patient. The present invention also relates to a breathing apparatus system intended for use in the respiratory care of a patient and including a ventilator and a tubing system.

2. Description of the Prior Art

The ability to determine and/or regulate the amount of breathing gas supplied to a patient is important in respiratory care. Determined and/or regulated volume is usually stipulated in volume per breath (tidal volume) or average volume received per unit of time (minute volume) Breathing gas is usually supplied to the patient by a ventilator and a tubing system. Since gases are compressible (elastic), the volume of gas in the tubing system must be taken into account. As a rule, the tubing system is also elastic, so the actual volume in the tubing system can vary with the pressure. Studies have shown that the mechanical elastic volume can constitute 25–40% of the total elastic volume.

Testing a breathing apparatus system (e.g. a ventilator and tubing system) before the patient is hooked up to it is common. Compensation for the elastic volume can then be made by an operator. This is particularly important when a specific tidal volume must be supplied to the patient in each breath.

It would be advantageous if these measurements also could be performed while the patient is connected to the breathing apparatus system for respiratory care, since conditions could change in the course of treatment. Changes might develop especially in peripheral devices, which constitute dead space for the system, such as humidifiers, dehumidifiers and nebulizers.

A major problem is to exclude the patient from volume determinations. Determinations would be erroneous if the patient's airways and lungs were allowed to interact with the tubing system during a volume determination.

Another problem is to establish total elastic volume in an effective fashion.

SUMMARY OF THE INVENTION

An object of the present invention is to provide a method for determining only the volume of a tubing system while a patient is connected to it.

Another object of the invention is to provide a method for determining the total elastic volume of a tubing system while the patient is connected to it.

Yet another object of the invention is to provide a breathing apparatus system in which the volume of the tubing system and the elastic volume of the tubing system can be established while the patient is connected to the tubing system.

The inventive methods and apparatus are based on the recognition that in the breathing or respiratory cycle there are (brief) periods when the flow of breathing gas to or from the patient is zero or close to zero. By utilizing these periods in the method according to the invention, the patient can be excluded from the volume determinations. Since the flow is zero, there is no interaction with the patient's lungs, nor will the additional supply of a gas for measuring the volume of the tubing system involve the patient in the measurement as long as the pressure in the tubing system is not affected. In the method according to the invention, an additional gas is supplied to the inlet of the tubing system at a predetermined flow rate, preferably at a constant rate. When this additional gas reaches the outlet of the tubing system, the volume of supplied additional gas can be calculated with a time integral of flow. The supplied volume of additional gas corresponds to the volume of the tubing system.

In an alternative embodiment of the inventive method, when the flow of breathing gas to or from the patient is virtually zero, such as during an inspiratory pause or during an expiratory pause, a predetermined flow of a first gas is added to the tubing system while maintaining constant pressure in the tubing system, a determination is made of when the first gas starts flowing out of the tubing system, the outflow of the first gas from the tubing system is measured, a predetermined flow of a second gas is then added to the tubing system while maintaining constant pressure in the tubing system, a determination is made of when the second gas starts flowing out of the tubing system, and a determination is then made of the out flowing first gas, this volume constituting the volume of the tubing system.

In principle, the only difference is that in the alternative method the volume of additional gas flowing out of the tubing system is determined after the tubing system has been filled with the additional gas.

Both methods can naturally be utilized at the same time by first determining the supplied volume and then determining the outflow volume. This then provides an additional check to show that the patient was not involved in the measurement in any way and that there was no leakage or the like.

In principle, the first additional gas supplied can be breathing gas but with a differing composition than is used, e.g. 5–10% more oxygen, or breathing gas containing some trace gas or a completely different gas mixture that is harmless to the patient, e.g. helium.

It is fully sufficient for only the very first part of the supplied additional gas to contain e.g. a trace gas or different composition. The trace gas (or different composition) only serves as a marker of the "column of air" introduced into the tubing system. Such a gas marker is sufficient, regardless of whether the volume is determined from the supplied volume or the outflow volume. Otherwise just breathing gas can be used. The risk of the patient inspiring anything other than breathing gas is then greatly reduced.

All the additional gas supplied during a determination of volume, however, can naturally have the same composition.

In a method for determining the elastic volume of a tubing system is achieved according to the invention, the volume of the system is measured at two different pressures, and the mechanical elastic volume is determined as the difference between the volumes found at the two different pressures.

Performing these measurements in the final phase of inspiration and final phase of expiration, respectively, is particularly important, since the pressure difference is then greatest while flow is at a minimum. Flow can even be zero, in the inspiratory pause and expiratory pause respectively.

In instances in which a continuous bias flow is used, this flow can either be compensated for in determinations or utilized when the gas/gases used in the determination is/are supplied.

In a breathing apparatus according to the present invention, including a ventilator and a tubing system, the ventilator has an inspiratory valve, an expiratory valve, at least one flow meter, at least one pressure meter, at least one gas meter, and a control unit which determines the volume of the tubing system according to one of the above-described embodiments of the inventive method.

Using the volume of the tubing system determined in accordance with the inventive method, the inventive breathing apparatus can undertake automatic determination of a factor for compensating for the volume of the tubing system in the volume of gas which is supplied to the patient for respiratory purposes.

DESCRIPTION OF THE PREFERRED EMBODIMENTS

Figure 1:
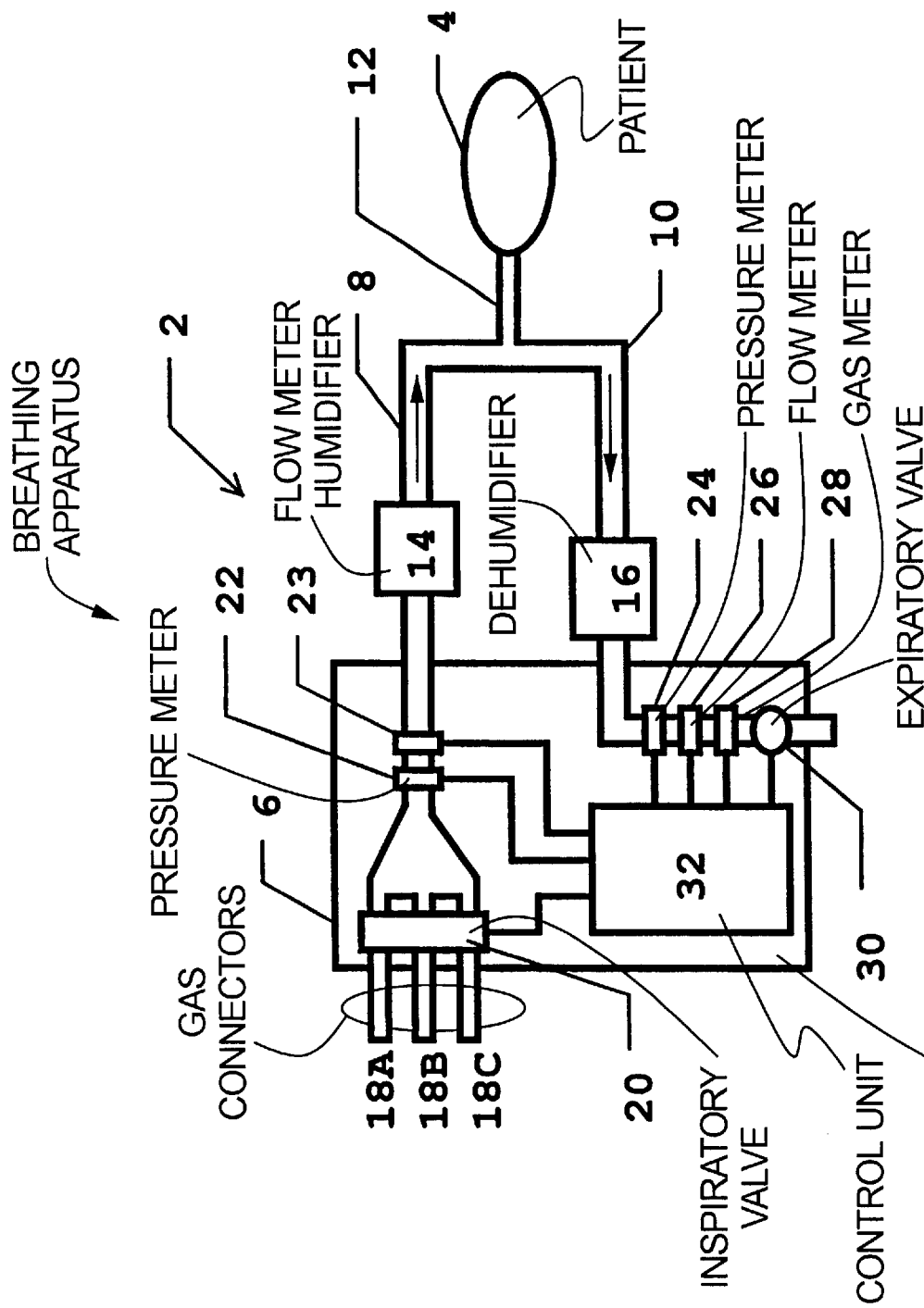
FIG. 1 shows one embodiment of a breathing apparatus system according to the invention.

FIG. 1 shows one embodiment of the breathing apparatus system according to the invention, designated 2. The breathing apparatus system 2 is connected to a patient 4 in order to provide the patient 4 with appropriate respiratory care including everything from supplying the patient 4 with appropriate breathing gas to exercising complete control over the breathing of the patient 4. The breathing apparatus system 2 basically includes a ventilator 6 and a tubing system 8, 10, 14, 16. The tubing system 8, 10, 14, 16 includes an inspiratory line 8 and an expiratory line 10 as basic elements. Various components can then be incorporated into the tubing system 8, 10, 14, 16. This embodiment shows a humidifier 14 and a dehumidifier 16. Other components can be used, however, such as a nebulizer, various filters etc. The tubing system 8, 10, 14, 16 is connected to the patient 4 by a patient tube 12.

Different gases can be connected to the ventilator 6 via a first gas connector 18A, a second gas connector 18B and a third gas connector 18C. For example, air can be supplied through the first gas connector 18A, oxygen through the second gas connector 18B and a non-toxic trace gas through the third gas connector 18C.

The connected gases can be regulated in appropriate proportions, pressures and flows by a valve unit 20 in order to generate a breathing gas for the patient 4. The valve unit 20 appropriately includes an inspiratory valve for each gas connector 18A, 18B, 18C. As a rule, the physician selects a mixture of air and oxygen. The example with a trace gas is used in this instance in performing the method according to the invention for determining the volume of the tubing system 8, 10, 14, 16 and/or an elastic volume of the tubing system 8, 10, 14, 16. The mixed gas is then carried past a first pressure meter 22 and a first flow meter 23 before it is fed into the inspiratory line 8.

A second pressure meter 24, a second flow meter 26, a gas meter 28 and an expiratory valve 30 are arranged on the expiratory side of the ventilator 6. A control unit 32 controls and monitors all functions in the ventilator 6.

Figure 2:
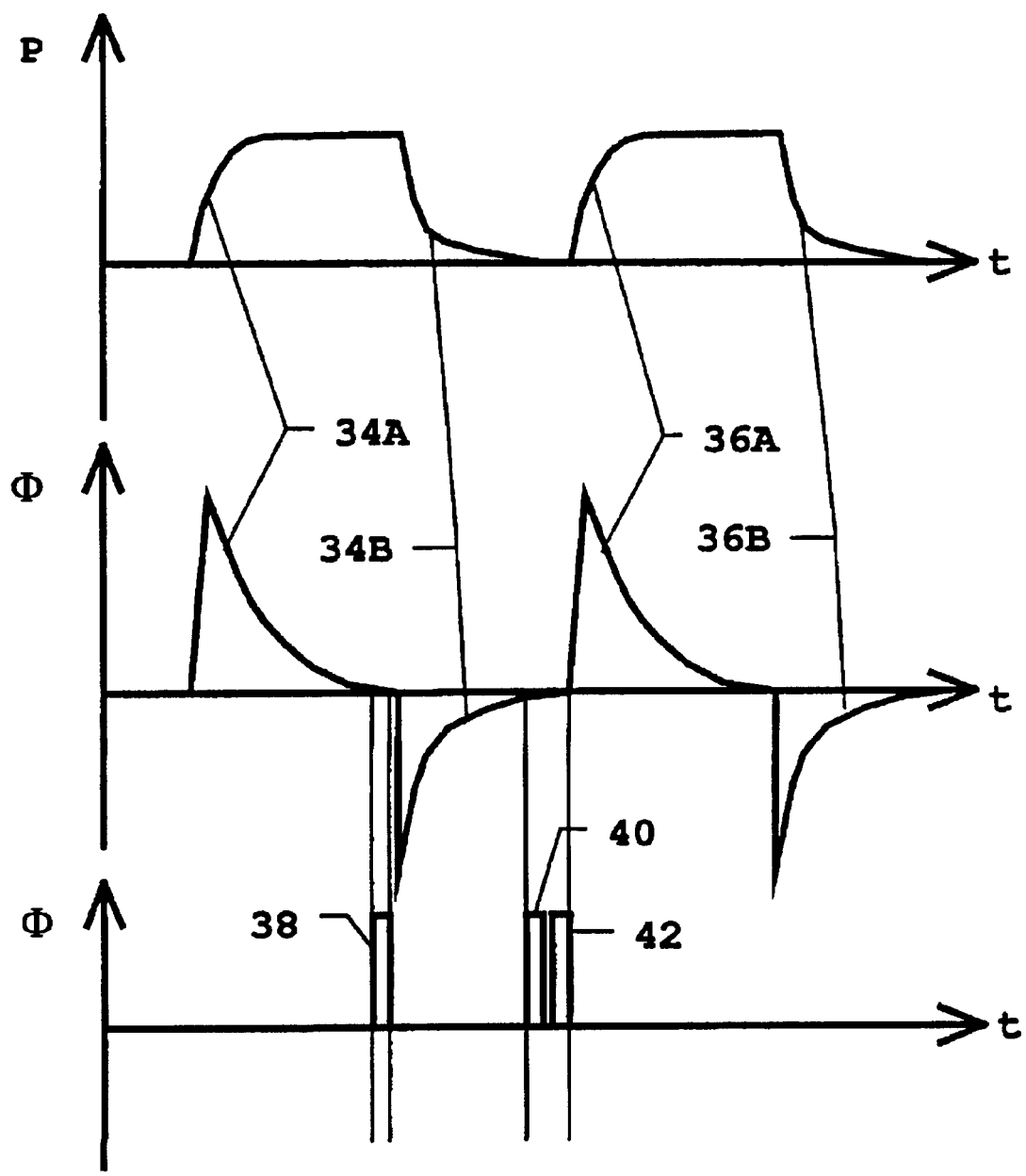
FIG. 2 is a diagram of a breathing cycle for use in explaining the inventive method and apparatus.

The main task of the breathing apparatus system 2 is to provide the patient 4 with appropriate respiratory care, e.g. by delivering breathing cycles as shown in the upper part of the diagram in FIG. 2 (the following refers both to FIG. 1 and FIG. 2). FIG. 2 shows two breathing cycles with the pressure (at the top) and flow (in the middle) of the breathing gas with respect to time. The first breathing cycle shows a first inspiration 34A and a first expiration 34B. Flow for the first inspiration 34A is shown as positive, since gas flowing to the patient 4 is defined as positive. Flow for the first expiration 34B is therefore negative. In the corresponding manner, a second inspiration 36A and a second expiration 36B are shown for the second breathing cycle.

The invention relates inter alia to a method for determining the volume of the tubing system 8, 10, 14, 16 while the patient 4 is connected, although without involvement of the lungs and airways of the patient 4 in the calculation. In principle, it is the volume between the valve unit 20 and the expiratory valve 30 that is of interest, but the vast majority of this volume is within the tubes and additional components. Since the patient line 12 is usually a tracheal tube inserted into the trachea of the patient 4, it is also excluded from calculations in the method according to the invention.

The lower part of the diagram in FIG. 2 shows how a first gas flow 38 of a first additional gas can be generated in the valve unit 20 in the ventilator 6 at a stage at which flow during the first inspiration 34A is virtually zero. To be more precise, it is the flow to the patient 4 that is close to zero.

When the expiratory valve 30 is simultaneously regulated so it discharges a flow corresponding to the first flow 38 generated by the valve unit 20, pressure in the tubing system 8, 10, 14, 16 remains unchanged. In this manner, the pressure gradient stays constant with respect to the patient 4, and only a minimal (if any) exchange of the first gas in the applied first flow of gas 38 can take place with the patient 4.

A comparison of the flow measured in the first flow meter 23 with the flow measured in the second flow meter 26 also offers an opportunity for checking to ensure that the patient 4 is not disrupting the measurement (both flow meters 23, 26 should record the same flow).

At least initially, the first gas has a different composition than the breathing gas used for the first inspiration 34A. This is for the purpose of obtaining a marker for the gas meter 28 in the expiratory section. The gas with this differing composition can be pure air, pure oxygen or any mixture of the involved gases other than the specific mixture used for the breathing gas. The gas meter 28 can then be an oxygen meter.

The marker in the first flow of gas 38 can also be a trace gas added to the breathing gas in a sufficient concentration. The gas meter 28 is then a meter for the specific trace gas.

Yet another option would be to add a gas with a completely different composition to obtain a marker, e.g. pure helium or helium and oxygen; in other words, replacing the breathing gas with another gas. Many options are therefore available to obtain a marker for the gas meter 28.

The most important thing is for the first gas to have a composition making it initially distinguishable from the breathing gas already in the tubing system 8, 10, 14, 16. Since the gas with a differing composition is only needed as a marker, it can therefore be used very briefly (in a small volume relative to the volume measured). The necessary amount will depend inter alia on the characteristics of the gas meter 28.

The gas with a differing composition, however, can also be 30 utilized for the entire volume determination.

When the first gas (i.e. the gas marker) reaches the gas meter 28 in the expiratory section, the entire tubing system 8, 10, 14, 16 will have become filled with gas (possibly with the same composition), and the addition of the first flow 38 can be terminated. The time integral of the first flow 38 then constitutes the volume of the tubing system 8, 10, 14, 16.

If the physician does not want the patient to receive any of the new gas mixture (when the same gas composition is utilized for the entire volume of the tubing system), a flushing flow of breathing gas can be introduced after the determination. This flushing flow can also be added at the onset of the first expiration 34B.

In the corresponding manner, the final phase of the first expiration 34B can be utilized for determining the volume when the flow gets close enough to zero. A first gas flow 40 of a first gas can be generated by the valve unit 20 in the ventilator 6. In the same way as described above, volume can be determined by establishing the volume of the first flow 40 required to fill the tubing system 8, 10, 14, 16.

An alternative (or complementing) method to determine the 20 volume will now be described in relation to the above. A second gas flow 42 of a second gas mixture can be generated by the valve unit 20 after the gas meter 28 has determined that the first gas flow 40 has filled the tubing system 8, 10, 14, 16. Once again, the idea is to have a gas marker for the gas meter 28 to be added to the second gas supplied to the tubing system 8, 10, 14, 16 in this phase of the determination.

As mentioned above, it is only necessary to have a different composition at the very onset of the supply of the second gas. When a trace gas is used at the very beginning of the supply of the first gas, the same trace gas can be used as a marker for the onset of the supply of the second gas flow.

If the first gas entirely consists of a gas composition differing from the breathing gas, the second gas mixture can consist of the breathing gas. Any gas with a composition differing from the first gas can naturally be used as the second gas.

At the same time, the second flow meter 26 measures flow on the expiratory side. The second gas flow 42 is added until the gas meter 28 determines that the second gas has filled the tubing system 8, 10, 14, 16 (i.e. when the new gas marker reaches the gas meter 28). The time integral of the measured flow of the first gas exiting from the tubing system 8, 10, 14, 16 corresponds to the volume of the tubing system 8, 10, 14, 16.

If only the volume of the tubing system 8, 10, 14, 16 is to be determined, one of the above-described methods will suffice (either at the end inspiration or at the end of expiration). When the second method is used, of course volume determinations can be made several times. First for the supplied volume of the first gas (equals the first method), then for the outflow volume of the first gas as described above, and lastly for the supplied volume of the second gas. This increases the accuracy of the determinations. Any distinctive variation between the determined volumes indicates a fault somewhere. Such faults could be simple ones, such as the patient coughing or interacting, or a temporary leakage. Such a variation also could be an indication of faults in the flow meter.

As shown above, measurements of the volume can be performed in a number of ways either close to or at the end of inspiration or close to or at the end of expiration. By establishing the volume of the tubing system 8, 10, 14, 16 at both these occasions, viz, the pressure prevailing at the end of inspiration and the pressure prevailing at the end of expiration, determinations can be made at two different pressures. Thus an elastic volume can be determined for the tubing system 8, 10, 14, 16, viz, the mechanical volume. The inherent elasticity of the tubes causes them to expand at higher pressures. The volume of the tubing system 8, 10, 14, 16 therefore increases at higher pressures. The difference between the two volume determinations, relative to the pressure gradient, establishes mechanical elasticity.

With the information supplied by the different measurements, a physician can set compensatory values for the pressures, flows and volumes of gas supplied to the patient 4.

Alternatively, the control unit 32 can be devised to perform automatic compensation according to the aforementioned volumes which are determined.

Using flow signals from the two flow meters 23, 26, compensation also can be made for any impact of the patient 4 (e.g. by coughing, commencing an inspiration or expiration at the "wrong" time, etc.) on these determinations. This compensation, however, does not yield volume determinations as accurate as those obtained when the patient 4 does not influence determinations.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for determining a volume of a tubing system connected to a ventilator and to a patient, comprising the steps of:

identifying a time at which a flow of breathing gas in said tubing system relative to a patient is substantially zero;

at said time, adding a predetermined flow of a gas as an inflow to said tubing system while maintaining a constant pressure in said tubing system;

determining when said gas added to said tubing system begins flowing out of said tubing system; and determining a volurrie of the inflow of said gas to said tubing system until said gas begins flowing out of said tubing system, and using said volume of said gas as said volume of said tubing system.

2. A method as claimed in claim 1 wherein the step of adding a predetermined flow of said gas comprises adding a predetermined flow of a gas having a composition, at least in an initial part of said gas, which is different from a composition of said breathing gas, said different composition serving as a marker for said gas which is added to said tubing system.

3. A method as claimed in claim 2 wherein the step of adding said predetermined flow of said gas comprises adding a predetermined flow of a gas having an initial part consisting of breathing gas plus a trace gas, and wherein the step of determining when said gas begins flowing out of said tubing system comprises measuring said trace gas in gas flowing out of said tubing system.

4. A method as claimed in claim 2 wherein the step of adding said predetermined flow of said gas comprises adding a predetermined flow of a gas having an initial part consisting of at least one component of said breathing gas but in a different concentration than in said breathing gas.

5. A method for determining a volume of a tubing system connected to a ventilator and to a patient, comprising the steps of:

identifying a time when a flow of breathing gas in said tubing system relative to a patient is substantially zero;

at said time, adding a predetermined flow of a first gas to the tubing system while maintaining a constant pressure in said tubing system;

measuring an outflow from said tubing system and determining when said first gas begins flowing out of said tubing system;

adding a predetermined flow of a second gas to said tubing system while maintaining said constant pressure in said tubing system;

determining when said second gas begins flowing out of said tubing system; and determining the volume of the first gas out flowing from said tubing system from when said first gas begins flowing out of said tubing system to when said second gas begins flowing out of said tubing system, and using said volume of said first gas out flowing from said tubing system as said volume of said tubing system.

6. A method as claimed in claim 5 wherein the step of adding a predetermined flow of said first gas comprises adding a predetermined flow of a first gas having a composition, at least in an initial part of said first gas, which is different from a composition of said breathing gas, said different composition serving as a marker for said first gas which is added to said tubing system.

7. A method as claimed in claim 6 wherein the step of adding said predetermined flow of said first gas comprises adding a predetermined flow of a first gas having an initial part consisting of breathing gas plus a trace gas, and wherein the step of determining when said first gas begins flowing out of said tubing system comprises measuring said trace gas in said first gas flowing out of said tubing system.

8. A method as claimed in claim 6 wherein the step of adding said predetermined flow of said first gas comprises adding a predetermined flow of a first gas having an initial part consisting of at least one component of said breathing gas but in a different concentration than in said breathing gas.

9. A method as claimed in claim 5 wherein the step of adding a predetermined flow of said second gas comprises adding a predetermined flow of a second gas having a composition, at least in an initial part of said second gas, which is different from a composition of said breathing gas, said different composition serving as a marker for said second gas which is added to said tubing system.

10. A method as claimed in claim 9 wherein the step of adding said predetermined flow of said second gas comprises adding a predetermined flow of a second gas having an initial part consisting of breathing gas plus a trace gas, and wherein the step of determining when said second gas begins flowing out of said tubing system comprises measuring said trace gas in said second gas flowing out of said tubing system.

11. A method as claimed in claim 9 wherein the step of adding said predetermined flow of said second gas comprises adding a predetermined flow of a second gas having an initial part consisting of at least one component of said breathing gas but in a different concentration than in said breathing gas.

12. A method as claimed in claim 5 wherein the step of adding a predetermined flow of said first gas comprises adding a predetermined flow of a first gas having a composition, in at least an initial part of said first gas, which is different from a composition of said breathing gas as a marker for said first gas, and wherein the step of adding a predetermined flow of said second gas comprises adding a predetermined flow of a second gas having a composition, at least in an initial part of said second gas, which is different from the composition of said breathing gas, as a marker for said second gas.

13. A method for determining an elastic volume of a tubing system connected to a ventilator and to a patient, comprising the steps of:

determining a volume of said tubing system at a first pressure during a first time in a breathing cycle at which a flow of breathing gas in said tubing system is substantially zero;

determining a volume of said tubing system at a second pressure at a second time in said breathing cycle at which flow of breathing gas relative to said patient in said tubing system is substantially zero; and determining an elastic volume of said tubing system from said volume determined at said first pressure and said volume determined at said second pressure.

14. A method as claimed in claim 13 wherein the step of determining said volume at said first pressure comprises the steps of:

at said first time, adding a predetermined flow of a gas to said tubing system while maintaining said first pressure in said tubing system;

determining when said gas added to said tubing system at said first time begins flowing out of said tubing system; and determining, as said volume determined at said first pressure, a volume of the gas added to said tubing system from said first time until said gas begins flowing out of said tubing system; and wherein the step of determining the volume of said tubing system as said second pressure comprises:

at said second time, adding a predetermined flow of a gas to said tubing system while maintaining said second pressure in said tubing system;

determining when said gas added to said tubing system at said second time begins flowing out of said tubing system; and determining, as said volume determined at said second pressure, a volume of the gas added to said tubing system from said second time until said gas begins flowing out of said tubing system.

15. A method as claimed in claim 14 wherein the step of adding a predetermined flow of a gas at said first time comprises adding a predetermined flow of a gas having a composition, at least in an initial part of said gas, which is different from a composition of said breathing gas, said different composition serving as a marker for said gas which is added to said tubing system at said first time.

16. A method as claimed in claim 15 wherein the step of adding said predetermined flow of said gas comprises adding a predetermined flow of a gas having an initial part consisting of breathing gas plus a trace gas, and wherein the step of determining when said gas added at said first time begins flowing out of said tubing system comprises measuring said trace gas in said gas, added at said first time, flowing out of said tubing system.

17. A method as claimed in claim 15 wherein the step of adding said predetermined flow of said gas comprises adding a predetermined flow of a gas having an initial part consisting of at least one component of said breathing gas but in a different concentration than in said breathing gas.

18. A method as claimed in claim 14 wherein the step of adding a predetermined flow of a gas at said second time comprises adding a predetermined flow of a gas having a composition, at least in an initial part of said gas, which is different from a composition of said breathing gas, said different composition serving as a marker for said gas which is added to said tubing system at said second time.

19. A method as claimed in claim 18 wherein the step of adding said predetermined flow of said gas comprises adding a predetermined flow of a gas having an initial part consisting of breathing gas plus a trace gas, and wherein the step of determining when said gas added at said second time begins flowing out of said tubing system comprises measuring said trace gas in said gas, added at said second time, flowing out of said tubing system.

20. A method as claimed in claim 18 wherein the step of adding said predetermined flow of said gas comprises adding a predetermined flow of a gas having an initial part consisting of at least one component of said breathing gas but in a different concentration than in said breathing gas.

21. A method as claimed in claim 14 wherein the step of adding a predetermined flow of a gas at said first time comprises adding a predetermined flow of a gas having a composition, in at least an initial part of said gas added at said first time, which is different from a composition of said breathing gas as a marker for said gas added at said first time, and wherein the step of adding a predetermined flow of a gas at said first time comprises adding a predetermined flow of a gas having a composition, at least in an initial part of said gas added at said second time, which is different from the composition of said breathing gas, as a marker for said gas added at said second time.

22. A method as claimed in claim 13 wherein the step of determining the volume of said tubing system at said first pressure comprises:
   at said first time, adding a predetermined flow of a first gas to the tubing system while maintaining said first pressure in said tubing system;
   measuring an outflow of said first gas from said tubing system and determining when said first gas, added at said first time, begins flowing out of said tubing system;
   adding a predetermined flow of a second gas to said tubing system while maintaining said first constant pressure in said tubing system;
   determining when said second gas begins flowing out of said tubing system; and
   determining, as said volume determined at said first pressure, the volume of the first gas out flowing from said tubing system from when said first gas begins flowing out of said tubing system to when said second gas begins flowing out of said tubing system;
and wherein the step of determining the volume of said tubing system at said second pressure comprises:
   at said second time, adding a predetermined flow of said first gas to the tubing system while maintaining said second pressure in said tubing system;
   measuring, after said second time, an outflow of said first gas from said tubing system and determining when said first gas, added at said second time, begins flowing out of said tubing system;
   after said second time, adding a predetermined flow of a second gas to said tubing system while maintaining said second pressure in said tubing system;
   after said second time, determining when said second gas begins flowing out of said tubing system; and
   after said second time, determining, as said volume determined at said second pressure, the volume of the first gas out flowing from said tubing system from when said first gas begins flowing out of said tubing system to when said second gas starts flowing out of said tubing system.

23. A method as claimed in claim 22 wherein each of the steps of adding a predetermined flow of said first gas, at said first and second times, respectively, comprises adding a predetermined flow of a first gas having a composition, at least in an initial part of said first gas, which is different from a composition of said breathing gas, said different composition serving as a marker for said first gas which is added to said tubing system.

24. A method as claimed in claim 23 wherein each of the steps of adding said predetermined flow of said first gas, at said first and second times, respectively, comprises adding a predetermined flow of a first gas having an initial part consisting of breathing gas plus a trace gas, and wherein each of the steps of determining when said first gas, after said first and second times, respectively, begins flowing out of said tubing system comprises measuring said trace gas in said first gas flowing out of said tubing system.

25. A method as claimed in claim 23 wherein the step of adding said predetermined flow of said first gas, at said first and second times, respectively, comprises adding a predetermined flow of a first gas having an initial part consisting of at least one component of said breathing gas but in a different concentration than in said breathing gas.

26. A method as claimed in claim 22 wherein each of the steps of adding a predetermined flow of said second gas, at said first and second times, respectively, comprises adding a predetermined flow of a second gas having a composition, at least in an initial part of said second gas, which is different from a composition of said breathing gas, said different composition serving as a marker for said second gas which is added to said tubing system.

27. A method as claimed in claim 26 wherein each of the steps of adding said predetermined flow of said second gas, at said first and second times, respectively, comprises adding a predetermined flow of a second gas having an initial part consisting of breathing gas plus a trace gas, and wherein each of the steps of determining when said second gas, after said first and second times, respectively, begins flowing out of said tubing system comprises measuring said trace gas in said second gas flowing out of said tubing system.

28. A method as claimed in claim 26 wherein each of the steps of adding said predetermined flow of said second gas, at said first and second times, respectively, comprises adding a predetermined flow of a second gas having an initial part consisting of at least one component of said breathing gas but in a different concentration than in said breathing gas.

29. A method as claimed in claim 22 wherein each of the steps of adding a predetermined flow of said first gas, at said first and second times, respectively, comprises adding a predetermined flow of a first gas having a composition, in at least an initial part of said first gas, which is different from a composition of said breathing gas as a marker for said first gas, and wherein each of the steps of adding a predetermined flow of said second gas, at said first and second times, respectively, comprises adding a predetermined flow of a second gas having a composition, at least in an initial part of said second gas, which is different from the composition of said breathing gas, as a marker for said second gas.

* * * * *